United States Patent [19]

Pettit

[11] Patent Number: 5,130,414

[45] Date of Patent: Jul. 14, 1992

[54] ISOLATION AND STRUCTURAL ELUCIDATION OF THE CYCLIC PEPTIDE HYMENISTATIN 1

[75] Inventor: George R. Pettit, Paradise Valley, Ariz.

[73] Assignee: Arizona Board of Regents, a body corporate of Arizona State University, Tempe, Ariz.

[21] Appl. No.: 443,882

[22] Filed: Nov. 30, 1989

[51] Int. Cl.[5] .................................................. C07K 7/64
[52] U.S. Cl. ................................... 530/321; 930/270; 930/DIG. 546
[58] Field of Search ............................... 530/321, 317

[56] References Cited

U.S. PATENT DOCUMENTS 4,977,138  12/1990  Okuhara et al. .................. 514/10

OTHER PUBLICATIONS

Pinedo, Med. Oncol. and Tumor Pharmacother. vol. 3, No. 2, pp. 63–69 (1986).
Suffness et al., J. Natural Products, vol. 45, pp. 1–14, 1982.

*Primary Examiner*—Y. Christina Chan
*Attorney, Agent, or Firm*—Richard R. Mybeck

[57] ABSTRACT

A new and demonstratably active cyclo-octapeptide is isolated from the South Pacific Ocean Hymeniacidon sp. and structurally elucidated. The substance, herein denominated Hymenistatin 1, demonstrated utility by inhibiting tumor growth when measured by the National Cancer Institute P388 leukemia cell line ($ED_{50} = 3.5$ μg/mL). Hymenistatin 1 has the following structure:

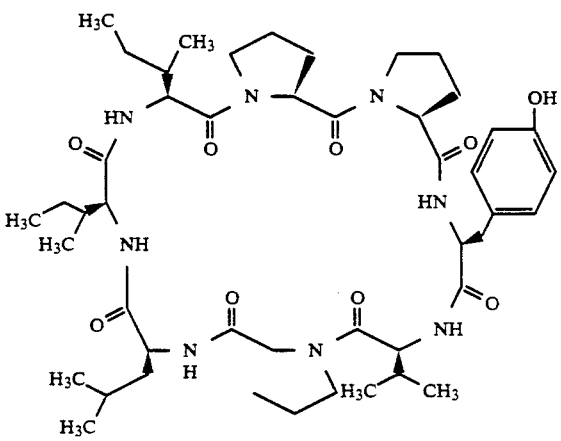

1 Claim, No Drawings

ISOLATION AND STRUCTURAL ELUCIDATION OF THE CYCLIC PEPTIDE HYMENISTATIN 1

The work described herein was partially funded under Grant CA-16049-05-12 awarded by the Division of Cancer Treatment, NCI, DHHS and by the Arizona Disease Control Research Commission.

INTRODUCTION

The present invention relates to the isolation and structural eludication of a new cyclo-octapeptide denominated "Hymenistatin 1". Hymenistatin 1 was isolated from the South Pacific Ocean sponge Hymeniacidon and found to demonstrate utility as a tumor growth inhibitor when measured by the P388 murine leukemia cell line (N.C.I. Protocol). Hymenistatin 1 has the general chemical structure:

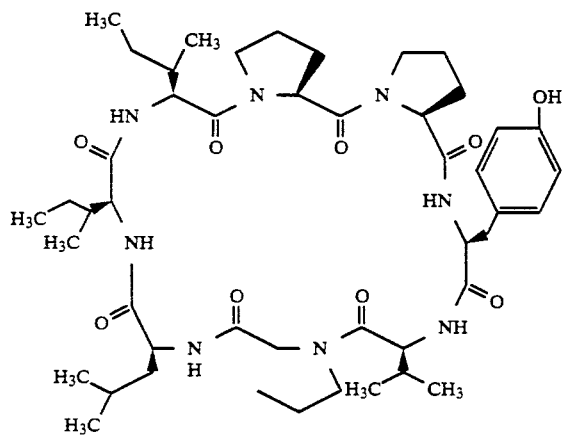

BACKGROUND OF THE INVENTION

Early investigations directed at isolation of antineoplastic constituents from marine sponges initially led to the geodiastatin proteins and later to a series of pyrrolactams. More recently, other promising leads have been detected in the Porifera phylum, including antineoplastic peptides. To date, only a few new amino acids, peptides and antineoplastic substances have been isolated from marine sponges. One of the Hymeniacidon sp. (Demospongiae Class) which was collected in Palau in 1979 yielded aqueous 2-propanol-methylene chloride extracts which demonstrated a 30% life extension against the U.S. National Cancer Institute's murine P388 lymphocytic leukemia (PS system). Bioassay directed isolation using the PS leukemia data led to isolation and identification of a new cytostatic peptide, herein denominated designated "Hymenistatin 1". The cyclo-octapeptide was isolated and subjected to structural elucidation.

In the continuing effort to locate and define various natural and synthetic substances for treatment of one or more varieties of cancer, research chemists continue to look at natural flora and fauna in an attempt to isolate and identify new substances which exhibit tumor growth inhibitory or antineoplastic activity while minimizing, if not totally eliminating, some of the severe side effects accompanying known chemotherapeutic agents.

It is in the further pursuit of these goals that marine species heretofore ignored are now being examined to determine whether they contain constituents which, when isolated, will exhibit useful biological properties such, for instance, as inhibiting tumor growth.

Accordingly, a principal object of the present invention is to provide new agents which possess useful biological properties.

Another object of the present invention is to provide methods and procedures for isolating antineoplastic substances from marine life in a form whereby they may be readily and usefully employed in the therapeutic treatment and management of one or more types of cancer which occur in human hosts and are manifested by malignant tumor growth.

A further object of the present invention is the provision of unique means and methods of isolating and elucidating the structure of a new cyclo-octapeptide from the South Pacific sponge Hymeniacidon sp.

These and still further objects of the present invention as shall hereinafter appear are readily fulfilled by the present invention in a remarkably unexpected manner as will be readily discerned from the following detailed description of exemplary embodiments thereof.

BRIEF SUMMARY OF THE INVENTION

The continuing search for biologically active substances from marine biotica in the South Pacific has led to the discovery of a new cyclo-octapeptide, herein denominated "Hymenistatin 1", which exhibits tumor growth inhibiting properties against the National Cancer Institute's murine P388 lymphocytic leukemia (PS system) showing $ED_{50}$ 3.5 µg/mL. Structural determination and absolute configuration was accomplished using high field NMR (400 MHz) and mass spectral techniques (FAB MS/MS) in conjunction with chiral gas chromatographic analysis. The direct correlation between the PS System and ultimate human efficacy of the substance as tested has been established (See: Vendetti and Abbot, Lloydia, 30, 322 et seq. (1967) and the references cited therein).

Hymenistatin I has the following general structure:

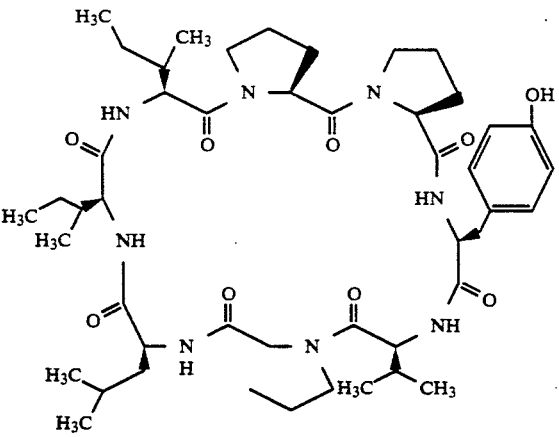

DESCRIPTION OF PREFERRED EMBODIMENTS

General Methods

Solvents used for chromatographic procedures were redistilled. The SEPHADEX LH-20 (25-100µ) employed for gel permeation and partition chromatography was obtained from Pharmacia Fine Chemicals AB, Uppsala, Sweden. GILSON FC-220 race track and FC-80 microfractionators connected to GILSON HM UV-visible detectors were used for chromatographic fractionation experiments, and column chromatographic procedures with silica gel utilizing the SILICA GEL 60 prepacked "LOBAR" columns supplied by E. Merck, Darmstadt, West Germany. The SILICA GEL GF UNIPLATES for TLC were obtained from Analtech Inc., Newark, Del. All TLC plates were viewed with uv light and/or developed with a ceric sulphate-sulfuric acid spray (heating to approximately 150° C. for 10 min).

The uncorrected melting points were observed using a KOFLER-type melting point apparatus. The uv spectrum was recorded using a HEWLETT-PACKARD 8450A uv-visible spectrophotometer equipped with a HP7225A plotter. Optical rotation and ir spectral data were obtained using a PERKIN-ELMER 241 polarimeter and a NICOLET MX-1 FTIR spectrophotometer, respectively. Mass spectra (70 eV and FAB) were recorded employing a KRATOS MS-50 spectrometer. The nmr experiments were conducted with a BRUKER WH-400 instrument and deuteriochloroform as solvent (TMS internal standard).

Animal Collection and Preliminary Experiments

In early 1979, approximately 2 kg (wet wt) of the sponge Hymeniacidon sp. (Hymeniacidonidae family, Halichondrida Order, Ceratinomorpha Subclass, Demospongiae Class) was collected by scuba near the Long Island (south side) in the Palau Archipelago, Western Caroline Islands. Taxonomic identification was conducted in the Smithsonian Institution where reference specimens are on file. The initial sample of Hymeniacidon sp. was preserved in 2-propanol-methylene chloride. Removal of solvent gave an extract that reached a confirmed level of activity against the U.S. National Cancer Institute's murine P388 lymphocytic leukemia (PS system) with 30% life extension at 5.5 mg/kg.

Animal Extraction and Solvent Partitioning

In March 1985, 218 kg (wet wt) of the Hymeniacidon sp. was recollected from the same area in Palau near the south side of Long Island and preserved in 2-propanol. The 2-propanol solution was later decanted and the sponge was re-extracted with the same alcohol. The first extract was reduced to a 50 liter water concentrate under partial vacuum and found to contain a considerable amount (1.2 kg) of a pale brown suspension (PS T/C toxic at $\geq$50 mg/kg), which was removed by centrifugation and decantation. The cream-colored aqueous phase was successively partitioned between methylene chloride (90 liters) and n-butanol (90 liters). Evaporation of solvent from each of the two combined organic extracts gave respectively, a very dark brown gel-like solid (180 g, PS ED$_{50}$ 1.8 $\mu$g/mL and T/C toxic at $\geq$50 mg/kg) and a pale brown amorphous solid (330 g, PS ED$_{50}$ 6.1 $\mu$g/mL and T/C toxic at $\geq$50 mg/kg). The remaining aqueous extract was found to be PS inactive and was discarded. A solution of the methylene chloride fraction (180 g) in 9:1 methanol-water (1 liter) was extracted with hexane (3$\times$1 liter). The methanol-water phase was diluted to 3:2 and extracted with methylene chloride. The resulting hexane (146 g), methylene chloride (20 g) and 3:2 methanol-water (14 g) fractions were concentrated and aliquots submitted for bioassay. Significant PS cytostatic activity (PS ED$_{50}$ 0.26 $\mu$g/mL) was found to reside in the methylene chloride extract.

Isolation of Hymenistatin 1.

In a typical series of procedures, the 20 g active methylene chloride fraction in 3:2 methylene chloride-methanol produced as described was chromatographed on a column of SEPHADEX LH-20 (1.2 kg; 20$\times$120 cm). While no pronounced separation of components was observed, a further concentration of active material (Fraction A, 18 g, PS ED$_{50}$ 1.6 $\mu$g/mL) was realized. Further partition chromatography on SEPHADEX LH-20 (1.2 kg; 20$\times$120 cm) and elution with 3:1:1 hexane-toluene-methanol gave active fractions B (0.50 g, PS ED$_{50}$ 2.6 $\mu$g/mL) and C (1.64 g, PS ED$_{50}$ 1.7 $\mu$g/mL) among eleven distinct composite fractions. Fractions B and C were combined and further separated in methanol on a SEPHADEX LH-20 column. Among the nine fraction groups obtained, a fraction labeled D (0.75 g, PS ED$_{50}$ 3.1 $\mu$g/mL) showed an almost single spot on tlc. Final purification was achieved utilizing a medium pressure (to 50 p.s.i.) liquid chromatography unit with a pre-packed SILICA GEL 60 column (2.5$\times$30 cm) and elution with 97.5–2.5 methylene chloride-methanol.

Hymenistatin 1 was obtained as a colorless, crystalline amorphous solid (49 mg, 3.1$\times$10$^{-5}$% yield), melting at 180°–182° C. [$\alpha$]$_D$-8.6° (c=1, CHCl$_3$); uv (CH$_3$OH) $\lambda$ max (log$\epsilon$), 222 (3.82), 278 (3.16) nm; ir (NaCl plate) 3320, 2960, 2920, 1680, 1617, 1517 cm$^{-1}$; ms (HRSP-SIMS), 893.5505 [M+H]$^+$ for C$_{47}$H$_{73}$N$_8$O$_8$, calcd. 893.5501; nmr (CDCl$_3$), $\delta$; Proline-a unit, $^1$H, 4.20 (H-2), 3.72 (H-5a), 3.38 (H-5b), 2.15 (H-3a), 2.11 (H-4a), 1.95 (H-4b), 1.93 (H-3b); $^{13}$C; 60.89 (C-2), 47.35 (C-5), 31.87 (C-3), 25.06 (C-4); Proline-b unit, $^1$H, 4.10 (dd, J=9.4, 3.5; H-2), 3.28 (H-5a), 3.21 (H-5b), 2.16 (H-3a), 1.77 (H-3b), 1.60 (H-4a), 0.85 (H-4b); $^{13}$C: 59.19 (C-2), 46.94 (C-5), 28.52 (C-3), 21.11 (C-4), Tyrosine unit, $^1$H, 8.70 (br s, OH), 7.03 (d, J=8.1; H-5), 6.84 (d, J=8.0; H-6), 4.22 (H-2), 3.29 (H-3a), 2.90 (t, J=13.0; H-3b), $^{13}$C, 156.56 (C-7), 129.67 (C-5, C-9), 127.00 (C-4), 115.94 (C-6, C-8), 58.13 (C-2), 36.67 (C-3), Valine unit, $^1$H: 7.58 (d, J=8.8; NH), 4.56 (t, J=5.9; H-2), 1.95 (H-3), 0.98 (6H; H-4, H-5); $^{13}$C: 56.29 (C-2), 31.67 (C-3), 19.29 (C-4), 18.19 (C-5). Proline c unit, $^1$H, 3.92 (H-5a), 3.79 (t, J=7.8; H-2), 3.68 (H-5b), 2.31 (H-3a), 2.08 (H-4a), 2.06 (H-4b), 1.91 (H-3b), $^{13}$C, 63.11 (C-2), 48.55 (C-5), 30.00 (C-3), 24.75 (C-4), Leucine unit, $^1$H, 6.25 (br s, NH), 3.98 (H-2), 1.96 (H-3a), 1.82 (H-3b), 1.55 (H-4), 0.93 (3H; d, J=6.3, H-6), 0.88 (3H, H-5), 13 C, 55.79 (C-2, 39.27 (C-3), 25.31 (C-4), 22.95 (C-6), 21.27 (C-5), Isoleucine-a unit, $^1$H, 7.70 (d, J=8.5,NH), 4.40 (t, J=8.5, H-2), 1.57 (H-3), 1.50 (H-4a), 1.15 (H-4b), 0.96, (3H; H-6), 0.87 (3H; H-5); $^{13}$C: 60 52 (C-2), 38.26 (C-3), 24.95 (C-4), 15.47 (C-6), 10.64 (C-5), Isoleucine-b unit, $^1$H, 7.40 (d, J=8.5, NH), 4.69 (t, J=9.0, H-2), 1.76 (H-3), 1.53 (H-4a), 1.05 (H-4b), 0.82 (3H; H-6), 0.80 (3H; H-5); $^{13}$C, 55.01 (C-2), 36.94 (C-3), 24.79 (C-4), 16.20 (C-6), 11.87 (C-5). Eight carbonyl $^{13}$C resonances appear at 172.72, 172.29, 172.10, 171.98, 171.95, 171.18, 170.35 (where no multiplicity is indicated it could not be determined due to overlapping signals).

Assignment of the Hymenistatin 1 Chiral Centers

The cyclo-octapeptide was hydrolyzed with 1:1 propionic acid 12N hydrochloric acid at 160° for 15 min. The corresponding amino acids were converted to N-pentafluropropionyl-isopropyl ester derivatives and configurations established by chiral capillary chromatography as described by Shaw and Cotter (See: Chromatographia, 21, 197 (1986)) using a Chirasil Val III column. Each amino acid component was found to belong to the S(L)-series.

In one practice of the present invention, initially, the isopropyl alcohol-water solution employed to preserve some 218 kg of the sponge was concentrated to 50 liters of an aqueous fraction containing a rather viscous beige colored suspension that required removal by centrifugation at 1000 G and filtration. The opaque, cream-colored aqueous portion was successively partitioned between methylene chloride followed by n-butanol to provide two active fractions as shown in the process scheme produced below.

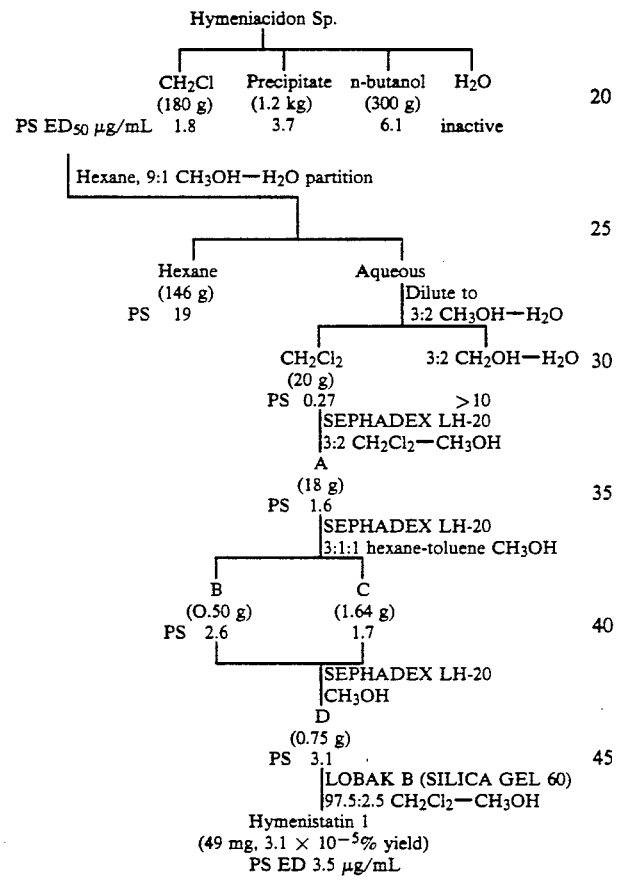

The PS active methylene chloride extract was partitioned between 9:1 methanol-water and hexane, followed by dilution to 3:2 methanol-water and partition with methylene chloride. Upon evaporation of the chlorocarbon an orange-colored solid was obtained which significantly inhibited the PS leukemia (PS $ED_{50}$ 0.26 μg/mL). Initial gel-permeation chromatographic separation of the methylene chloride-soluble fraction on SEPHADEX LH-20 and elution with 3:2 methylene chloride-methanol led to a further concentration of activity in Fraction A. A better separation was achieved employing partition chromatography on SEPHADEX LH-20 with 3:1:1 hexane-toluene-methanol to provide fractions B and C. These two principal active fractions B and C were then combined and separated on a column of SEPHADEX LH-20 in methanol to provide Fraction D. The nearly pure cytostatic constituent obtained by this means was chromatographed using a SILICA GEL 60 LOBAR B column. Elution with 97.5:2.5 methylene chloride-methanol afforded the cell growth inhibitory (PS $ED_{50}$ 3.5 μg/mL) biosynthetic product herein designated Hymenistatin 1.

Mass spectral measurements of Hymenistatin 1, as reported herein, indicated the presence of eight nitrogen atoms, which with eight amide carbonyls observed in the $^{13}C$ nmr spectrum, indicated an octapeptide. The relatively high intensity of the molecular ion (base peak) observed in the EIMS spectrum suggested that the presumed octapeptide might by cyclic. Extensive application of 2-D nmr techniques were next used to determine the identity of the eight amino acid units. The 400 MHz $^{1}H$-nmr spectrum clearly showed the presence of only five ( amide protons. By following the spin systems of these protons using $^{1}H,^{1}H$-COSY and $^{1}H,^{1}H$ relayed COSY, these amino acids were determined to be valine, leucine, tyrosine and two isoleucine units. Utilization of $^{1}H,^{13}C$-COSY and $^{1}H,^{1}H,^{13}C$-RELAY showed that the remaining nmr signals consisted of three independent spin systems of the type X-CH-CH$_2$-CH$_2$-X typical of proline. The eight amino acid units accounted for the observed accurate-mass molecular weight. Actual sequence of the amino acids was ascertained from ID-nOe (nuclear Overhauser effects) experiments as shown below.

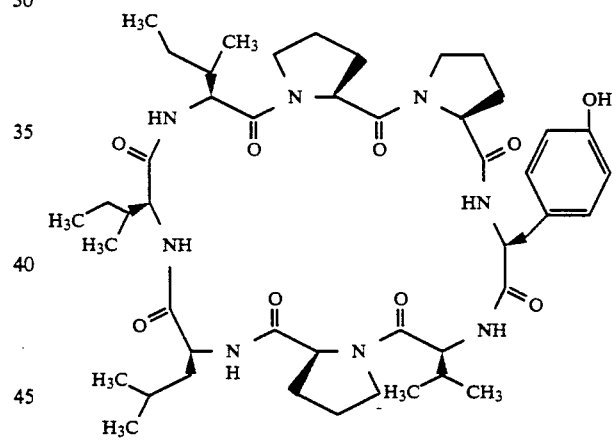

In order to further corroborate the proposed structure, positive ion FAB MS/MS was pursued. As shown below, protonation at each proline nitrogen afforded three different linear peptide ions in the mass spectrum noted as a, b and c. All but one of the ions predicted from their fragmentation was also observed, thereby confirming the structure assigned Hymenistatin 1 as shown herein. The absolute configuration of each chiral center was assigned using chiral GC analysis (Chirasil-Val III column) of the peptide hydrolysate following preparation of the N-pentafluoropropionylisopropyl ester derivatives. All of the amino acid units were found to bear the L-configuration.

Hymenistatin 1 peptide sequence determination by FAB ms/ms.

cyclo [Pro$^a$-Pro$^b$-Tyr-Val-Pro$^c$-Leu-Ili-Ile]

Observed mass spectral fragmentation resulting from protonation at proline (indicated by a, b, or c):

a, ProH⁺—Pro—Tyr—Val—Pro—Leu—Ile—Ile m/z   195  358  457  554  667  780  from ms of m/z 780 b, ProH⁺—Tyr—Val—Pro—Leu—Ile—Ile—Pro m/z   261  360  457  570  683  796  from ms of m/z 796 c, ProH⁺—Leu—Ile—Ile—Pro—Pro—Tyr—Val m/z   211  324  437  534       794  from ms of m/z 794

To further aid in the understanding of the present invention and not by way of limitation, the following examples are prescribed.

EXAMPLE I

Hymeniacidon sp. was collected (218 kg, wet) and preserved in 2-propanol. The 2-propanol solution was decanted and the sponge was reextracted with 2-propanol. The first extract was reduced to a 50 liter water concentrate under partial vacuum which contained a pale brown suspension which was removed therefrom by centrifugation and decantation leaving a cream colored aqueous phase.

EXAMPLE II

The cream colored aqueous phase produced by Example I was partitioned between methylene chloride (90 liters) and n-butanol (90 liters). Evaporation of solvent from each of the two combined organic extracts gave a very dark brown gel-like solid (180 g, PS $ED_{50}$ 1.8 μg/mL and T/C 105 at 50 mg/kg) and a pale brown amorphous solid (330 g. PS $ED_{50}$ 6.1 μg/mL and T/C toxic at >50 mg/kg).

EXAMPLE III

The methylene chloride fraction (180 g) produced according to Example II was disposed in 9:1 methanol-water solution (1 liter) and extracted with hexane (3×1 liter). The methanol-water phase was diluted to 3:2 and extracted with methylene chloride.

The resulting hexane (146 g), methylene chloride (20 g) and 3:2 methanol-water (14 g) fractions were concentrated and aliquots thereof subjected to bioassay. The methylene chloride extract was found to possess significant PS cytostatic activity (PS $ED_{50}$ 0.26 μg/mL).

EXAMPLE IV

The methylene chloride fraction (20 g) produced according to Example III was dispersed in 3:2 methylene chloride-methanol and thereafter chromatographed on a column of SEPHADEX LH-20 (1.2 kg; 20×120 cm). A further concentration of active material occurred as Fraction A. (18g, PS $ED_{50}$ 1.6 μg/mL). Additional partition chromatography on SEPHADEX LH-20 (1.2 kg; 20×120 cm) and elution with 3:1:1 hexane-toluene-methanol produced, inter alia, Fraction B (0.5 g, PS $ED_{50}$ 2.5 μg/mL) and actual Fraction C (1.64 g, PS $ED_{50}$ 1.7 μg/mL).

EXAMPLE V

Fraction B and C, obtained from Example IV, were combined and further separated in methanol on a SEPHADEX LH-20 column into nine separate fractions. Among the fractions obtained, a fraction designated D (0.75 g, PS $ED_{50}$ 3.1 μg/mL) showed an almost single spot on tlc.

EXAMPLE VI

Fraction D obtained from Example V was further purified using a medium pressure (up to 50 psi) liquid chromatography unit with a pre-packed SILICA GEL 60 column (2.5×30 cm) and eluted with 97.5-2.5 methylene chloride-methanol. Hymenistatin 1 was obtained as a colorless, crystalline amorphous solid (49 mg, $3.1 \times 10^{-5}$% yield) melting at 180°-182° C.

From the foregoing, it is readily apparent that an invention has been herein described and illustrated which fulfills all of the aforementioned objectives in a remarkably unexpected fashion. It is, of course, understood that such modifications, alterations, and adaptations as may readily occur to the artisan confronted with this disclosure are intended within the spirit of this invention which is limited solely by the scope of the claims appended hereto.

Accordingly, what is claimed is:

1. A compound denominated Hymenistatin 1 having the general structural formula.

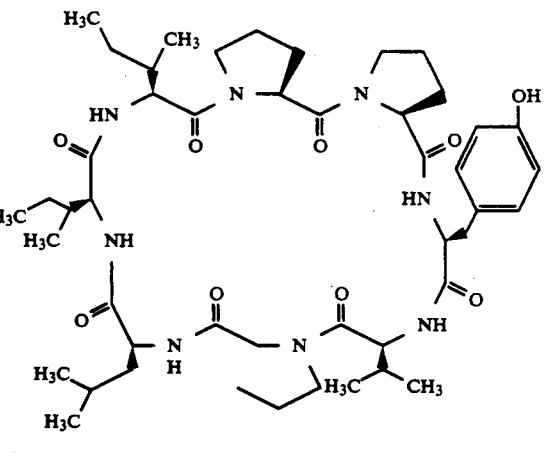

UNITED STATES PATENT AND TRADEMARK OFFICE
CERTIFICATE OF CORRECTION

PATENT NO. : 5,130,414

DATED : July 14, 1992

INVENTOR(S) : George R. Pettit

It is certified that error appears in the above-identified patent and that said Letters Patent is hereby corrected as shown below:

On the title page, following the Abstract; Column 1, line 20; Column 2, line 41; and Column 8, line 38, replace the diagram with the following:

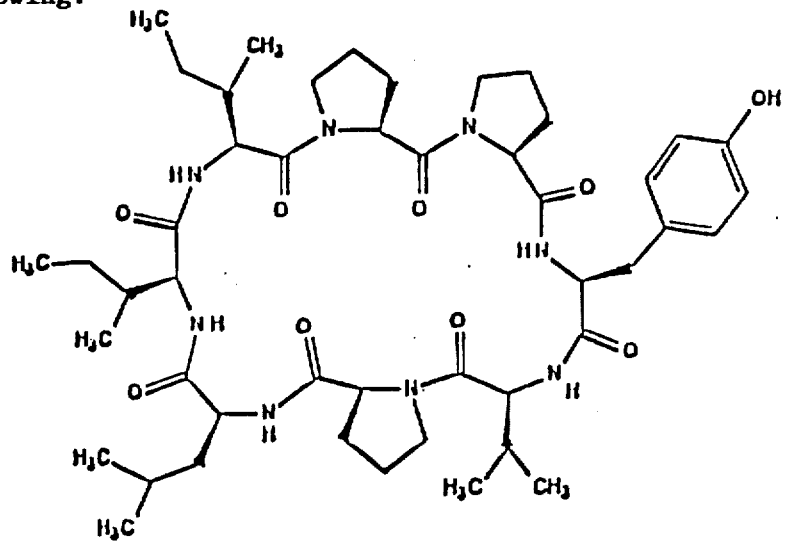

Signed and Sealed this

Twenty-first Day of September, 1993

Attest:

BRUCE LEHMAN

Attesting Officer  Commissioner of Patents and Trademarks